US009656980B2

(12) United States Patent
Madon et al.

(10) Patent No.: US 9,656,980 B2
(45) Date of Patent: May 23, 2017

(54) CATALYST FOR TETRAHYDROFURAN SYNTHESIS

(71) Applicant: BASF Corporation, Florham Park, NJ (US)

(72) Inventors: Rostam Jal Madon, Flemington, NJ (US); Rolf Pinkos, Ludwigshafen (DE); Olga Osetska, Ludwigshafen (DE); Deepak S Thakur, Beachwood, OH (US); Ronald L. Jagta, Beachwood, OH (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

(21) Appl. No.: 14/550,316

(22) Filed: Nov. 21, 2014

(65) Prior Publication Data
US 2015/0105568 A1 Apr. 16, 2015

Related U.S. Application Data

(63) Continuation of application No. 13/851,562, filed on Mar. 27, 2013.
(60) Provisional application No. 61/617,992, filed on Mar. 30, 2012.

(51) Int. Cl.
C07D 307/08 (2006.01)
B01J 21/12 (2006.01)
B01J 37/16 (2006.01)
B01J 37/18 (2006.01)
B01J 29/46 (2006.01)
B01J 37/02 (2006.01)
B01J 21/04 (2006.01)
B01J 23/72 (2006.01)
B01J 35/00 (2006.01)

(52) U.S. Cl.
CPC ............ C07D 307/08 (2013.01); B01J 21/04 (2013.01); B01J 21/12 (2013.01); B01J 23/72 (2013.01); B01J 29/46 (2013.01); B01J 37/0201 (2013.01); B01J 37/16 (2013.01); B01J 37/18 (2013.01); B01J 35/002 (2013.01); B01J 2229/186 (2013.01); B01J 2229/42 (2013.01)

(58) Field of Classification Search
CPC ..... C07D 307/08; B01J 29/46; B01J 37/0201; B01J 37/16; B01J 37/18; B01J 21/12; B01J 21/04; B01J 23/72; B01J 2229/186; B01J 2229/42; B01J 35/002
See application file for complete search history.

(56) References Cited

U.S. PATENT DOCUMENTS 3,338,666 A 8/1967 Sanchez
4,006,104 A 2/1977 Michalczyk et al.
4,199,555 A 4/1980 Itoh
4,739,122 A 4/1988 Letts
4,919,765 A 4/1990 Wilkes et al.
5,403,962 A 4/1995 Schneider et al.
6,350,924 B1 2/2002 Fischer et al.
6,433,192 B1 8/2002 Fischer et al.
6,809,217 B1 10/2004 Colley et al.
6,936,727 B2 8/2005 Sutton et al.
7,087,802 B2 8/2006 Schindler et al.
7,442,810 B2 10/2008 Roesch et al.
7,598,404 B2 10/2009 Backes et al.
8,129,548 B2 3/2012 Wood et al.
2002/0040161 A1 4/2002 Ryan
2007/0135650 A1 6/2007 Rosch et al.
2009/0317672 A1 12/2009 Yonemura
2011/0092721 A1 4/2011 Wood et al.
2011/0302826 A1* 12/2011 Gruter ............................ 44/350

FOREIGN PATENT DOCUMENTS

CN 1890231 A 1/2007
CN 101307042 11/2008
GB 2207914 2/1989
WO WO-01/17673 A1 3/2001
WO WO-2005/058853 6/2005
WO 2009106877 9/2009

OTHER PUBLICATIONS

Vimont, A., "Infrared spectroscopic study on the surface properties of γ-gallium oxide as compared to those of γ-alumina." The Journal of Physical Chemistry B 109.19 (2005): 9656-9664.*
Ding, G., "Vapour phase hydrogenolysis of biomass-derived diethyl succinate to tetrahydrofuran over CuO_ ZnO/solid acid bifunctional catalysts." Journal of chemical technology and biotechnology 86.2 (2011): 231-237.*
Clark, J.H., Kirk Othmer Encyclopedia of Chemical Technology—Supported Catalysts (1999) p. 1-37.
Majors, P.O., "Surface site distributions by solid-state multinuclear NMR spectroscopy. Pyridine binding to. gamma.-alumina by nitrogen-15 and deuterium NMR." Journal of the American Chemical Society 109.6 (1987): 1648-1653.
Parry, E. P.,"An infrared study of pyridine adsorbed on acidic solids. Characterization of surface acidity." Journal of Catalysis 2.5 (1963): 371-379.
Tanabe, K., et al. "Acidic Property and Catalytic Activity of Ti2—Zn0." Bull. Chem. Soc. Japan 45 (1972): 47-51.
Boumaza, A., "Transition alumina phases induced by heat treatment of boehmite: An X-raydiffraction and infrared spectroscopy study," Journal of Solid State Chemistry 182 (2009): 1171-1176.
PCT International Search Report & Written Opinion in PCT/US2013/034230 mailed Jul. 4, 2013, 14 pgs.
(Continued)

Primary Examiner — Samantha Shterengarts
Assistant Examiner — Matt Mauro
(74) Attorney, Agent, or Firm — Foley & Lardner LLP

(57) ABSTRACT

Provided are catalysts suitable for the production of tetrahydrofuran from 1,4-butanediol. Also provided are methods of use of these catalyst, as well as catalyst systems. The catalysts described herein contain only Lewis acidity, but not Broǿnsted acidity, which results in decreased production of ether byproducts.

6 Claims, No Drawings

(56) References Cited

OTHER PUBLICATIONS

Guo, P. J. et al., "One-step hydrogenolysis of dimethyl maleate to tetrahydrofuran over chromium-modified Cu—B/y-Al2O3 catalysts", Journal of Molecular Catalysis A: Chemical, vol. 256 2006, 164-170.
Muller, Steffan P. et al., "Extrusion of Cu/ZnO catalysts for the single-stage gas-phase processing of dimethyl maleate to tetrahydrofuran", Journal of Catalysis, vol. 218 2003, 419-426.
First Office Action received for Chinese Patent Application No. 201380021760.4 issued Nov. 23, 2015, 10 pages with English translation.
Cunzhang Xing, Experiments of Applied Chemistry, Chemical Industry Press, pp. 135-136, Jul. 31, 2010. (Translation of experimental principle, paragraph 1, provided).
Deutschmann, O., "Heterogeneous catalysis and solid catalysts." Ullmann's Encyclopedia of Industrial Chemistry (2009). (68 pages).
Henkel, K-D.,"Reactor types and their industrial applications." Ullmann's Encyclopedia of Industrial Chemistry (2000). (36 pages).
Second Office Action in Chinese Patent Application No. 201380021760.4, issued Sep. 19, 2016, 12 pages with English translation.
Non-Final Office Action in U.S. Appl. No. 14/705,613, mailed on Nov. 3, 2016 (11 pages).

* cited by examiner

CATALYST FOR TETRAHYDROFURAN SYNTHESIS

CROSS-REFERENCE TO RELATED APPLICATIONS

This application is a continuation of U.S. Ser. No. 13/203,577, filed Mar. 27, 2013, which claims priority from U.S. Provisional No. 61/617,992, filed Mar. 30, 2012, the entire contents of which are hereby incorporated by reference.

FIELD

Embodiments of the present invention generally relate catalysts suitable for tetrahydrofuran synthesis from 1,4-butanediol. Specific embodiments pertain to catalysts suitable for such processes, and processes for synthesizing tetrahydrofuran.

BACKGROUND

Tetrahydrofuran (THF) is a useful chemical that can be used as a high-purity solvent, or be polymerized to form polytetramethylene oxide. This polymer can be used to make elastomeric polyurethane fibers like Spandex. Maleic and/or succinic diesters can be hydrogenated over copper-based catalysts in the gas phase at elevated pressures to give mixtures of THF, gamma-butyrolactone (GBL), and 1,4-butanediol (BDO). Byproducts of this hydrogenation/hydrogenolysis process include n-butanol and its derivatives, including dimethyl ether, dibutyl ether, butyraldehyde, and linear ethers of butanol with the esterifying alcohol.

The main products of this process are desired intermediates for important and useful chemicals. GBL is used for preparing pyrrolidones such as pyrrolidone itself and N-methylpyrrolidone. BDO finds use in the production of polyurethanes and polyesters, and, importantly, is used for preparing THF. Typically, the complete process for the synthesis of THF is as follows: First, maleic anhydride undergoes esterification with methanol (or ethanol) to form dimethyl maleate (DMM). Then, DMM is hydrogenated to form BDO and methanol (or ethanol). This step has been carried out using a catalyst comprising copper, manganese and alumina. Finally, the resultant stream containing BDO is converted, to whatever extent required, via dehydration and ring closure, to THF. This step is typically carried out using copper on alumina catalyst.

However, during the DMM to BDO reaction, several unwanted byproducts are formed that include butanol, and butyraldehyde. The total amount of THF formed from BDO and the total consumption of BDO to THF depends on the reaction conditions; and total amounts of THF from 10 mol % and higher may be formed. However, in such a reaction environment, due to the presence of butanol and methanol, the THF formed is accompanied by the formation of small amounts of butyl methyl ether (BME). The various uses of THF require very pure THF that is especially free from even low levels of BME or dimethyl ether (DME). BME even in very small amounts affects the use of THF, as it is very difficult to distill from the desired THF product. This difficulty in distillation can lead to great expense to obtain the necessary THF purity.

Thus, there is a need for a catalyst that can convert 1,4-butanediol to THF while minimizing the amount of byproducts (particularly BME), such that the cost in distillation of the THF can be greatly reduced.

SUMMARY OF THE INVENTION

One aspect of the invention relates to a catalyst composition for the synthesis of tetrahydrofuran. The catalyst composition comprises about 3 to about 50 wt % copper oxide on a gamma-alumina support, wherein the catalyst composition comprises less than about 1.5 wt % silica and the catalyst composition has Lewis acidity and no, or substantially no, Brønsted acidity. In one embodiment, the catalyst composition wherein the catalyst composition has substantially only Lewis acidity determinable from IR absorption spectra of pyridine adsorbed on the catalyst. In another embodiment, the gamma-alumina contains substantially no stabilizers.

The amount of silica can be varied. Thus, in one embodiment, the catalyst composition comprises less than about 1 wt % silica. In another embodiment, the catalyst composition comprises less than about 0.5 wt % silica. In yet another embodiment, the catalyst composition comprises substantially no silica.

In other embodiment, the amount of copper oxide can also be varied. Accordingly, in one or more embodiments, the catalyst composition contains from about 3 to about 30 wt % copper oxide. In further embodiments, the catalyst composition contains from about 10 to about 15 wt % copper oxide.

A second aspect of the invention relates to a method of synthesizing tetrahydrofuran. The method comprises contacting a stream comprising 1,4-butanediol with a catalyst composition comprising about 3 to about 50 wt % copper oxide on a gamma-alumina support, wherein the catalyst composition comprises less than about 1.5 wt % silica, and with the proviso that the catalyst composition has Lewis acidity and no or substantially no Brønsted acidity, thereby converting at least a portion of the 1,4-butanediol into tetrahydrofuran. In one embodiment, the catalyst composition wherein the catalyst composition has substantially only Lewis acidity determinable from IR absorption spectra of pyridine adsorbed on the catalyst. In another embodiment, the gamma-alumina contains substantially no stabilizers. In yet another embodiment, the method further comprises reducing the CuO to copper metal prior to contacting the catalyst composition with a stream comprising 1,4-butanediol.

As with before, the amount of silica can be varied. Thus, in one embodiment, the catalyst composition comprises less than about 1 wt % silica. In another embodiment, the catalyst composition comprises less than about 0.5 wt % silica. In yet another embodiment, the catalyst composition comprises substantially no silica.

Similarly, in other embodiment, the amount of copper oxide can also be varied. Accordingly, in one or more embodiments, the catalyst composition contains from about 3 to about 30 wt % copper oxide. In further embodiments, the catalyst composition contains from about 10 to about 15 wt % copper oxide.

A third aspect of the invention pertains to a catalyst system for the synthesis of tetrahydrofuran from maleic anhydride. The system comprises a first catalyst composition effective to convert dimethyl maleate and dimethyl succinate to 1,4-butanediol and methanol, and a second catalyst composition comprising about 3 to about 50 wt % copper oxide on a gamma-alumina support, wherein the catalyst composition comprises less than about 1.5 wt % silica, and the catalyst composition has Lewis acidity and no or substantially no Brønsted acidity. In one embodiment, the copper oxide is reduced to copper metal. In another embodiment, the catalyst composition wherein the catalyst composition has substantially only Lewis acidity determinable from IR absorption spectra of pyridine adsorbed on the catalyst. In yet another embodiment, the gamma-alumina contains substantially no stabilizers.

The setup of the catalyst system can be varied. In one embodiment, the first and second catalyst compositions are in pellet form in a fixed bed reactor. In a further embodiment, the fixed bed reactor contains a layer of the first catalyst composition over a layer of the second catalyst composition. In yet a further embodiment, the system further comprises a protective layer over the layer of the first catalyst composition, which may comprise copper and chromium.

In an alternative variant, the first and second catalyst compositions are in pellet form in separate reactors. In a further embodiment of this variant, the system further comprises a protective layer over the first catalyst composition, which may comprise copper and chromium.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Aspects of this invention pertain to an acid catalyst suitable for converting BDO to THF. Currently used catalysts for this process also give ether byproducts from previous steps in THF synthesis to give ethers like BME and DME. It has been discovered that the solid acid catalyst that converts BDO to THF in the commercial stream is critical in BME formation. It has also been discovered that if this acid catalyst contains only Lewis acidity (as opposed to Brønsted acidity) in the form of gamma alumina, then the BME and DME formed is minimal compared to catalysts that contain Brønsted acidity. The amount of BME and/or DME can also be reduced by controlling the amount of silica or stabilizers in the gamma alumina. Thus, one aspect of the invention relates to a catalyst comprising copper supported on gamma alumina which contains only Lewis acidity. Other embodiments do not contain additives to the alumina, such as silica.

Accordingly, one aspect of the invention relates to a catalyst composition for the synthesis of tetrahydrofuran, the catalyst composition comprising about 3 to about 50 wt % copper oxide on a gamma-alumina support, wherein the catalyst composition comprises less than about 1.5 wt % silica and the catalyst composition has Lewis acidity and no, or substantially no, Brønsted acidity. In one or more embodiments, the catalyst composition has substantially only Lewis acidity determinable from IR absorption spectra of pyridine adsorbed on the catalyst.

There are many variants of this aspect of the invention. For example, the amount of copper can be varied. Thus, in one or more embodiments, the catalyst composition contains from about 3 to about 30 wt % copper oxide, or more specifically about 5 to about 50. In other embodiments, the catalyst composition contains from about 5 to about 20, or 10 to about 15 wt % copper oxide.

In yet other embodiments, the amount of silica can be varied. For example, in one or more embodiments, the catalyst composition comprises less than about 1 wt %, 0.5 wt %, 0.25 wt %, or 0.1 wt % silica. In other embodiments, the catalyst composition comprises no silica, or substantially no silica.

The dehydration catalyst used according to the present invention has no Brønsted acidity, but does have Lewis acidity. As used herein, a "Brønsted acid" is a chemical species that donates a proton to a Brønsted base. Brønsted acidity is distinguished from Lewis acidity, in that a "Lewis acid" is a chemical species that accepts an electron pair from another species. In some embodiments, "no Brønsted acidity" means that there is no detectable Brønsted acidity using the diffuse reflectance Fourier infrared transform spectroscopy (DRIFTS) procedure described below in the Examples section. This procedure measures the relative amounts of pyridine adsorbed on Brønsted and Lewis sites on solids.

One can avoid the introduction of Brønsted acidity by limiting the additives of the catalyst. In fact, in one embodiment, the gamma-alumina contains substantially no additives, including stabilizers. Such stabilizers include oxides of various metals (i.e., lanthanum, zirconium, etc.) Other components which can add Brønsted acidity to the catalyst composition include, but are not limited to, aluminosilicate zeolites (i.e., ZSM-5), other microporous materials (i.e., SAPOs, ALPOs etc.), and heteropolyacids. Additionally, if the amount of silica in gamma-alumina is too high, this can cause the catalyst composition to have Brønsted acidity. In one or more embodiments, some stabilizers may increase Lewis acidity.

The catalyst described herein can be prepared via techniques well known in the art. For example, copper can be put onto gamma-alumina via the incipient wetness technique using an aqueous solution of $Cu(NO_3)_2$ up to about 95% of the pore volume. The catalyst can then be calcined to decompose the nitrate to the oxide form. Suitable calcination temperatures range from about 300 to about 500° C. In one embodiment, the calcination temperature is about 350° C. The catalyst composition can then be formed into any suitable shape. In a particular embodiment, the catalyst composition is formed into pellets. In an even more particular embodiment, pellets have a size of about ⅛" by ⅛". The catalyst is usually reduced in $H_2$ containing gas to obtain metallic copper prior to use.

As discussed above, embodiments of the catalysts described herein are useful for the synthesis of THF. Accordingly, another aspect of the invention relate to processes for preparing (THF) in a mixture with gamma-butyrolactone and 1,4-butanediol. In such a process for synthesizing tetrahydrofuran, the method comprises contacting a stream comprising 1,4-butanediol with a catalyst composition comprising about 3 to about 50 wt % copper oxide on a gamma-alumina support, wherein the catalyst composition comprises less than about 1.5 wt % silica, and with the proviso that the catalyst composition has Lewis acidity and no Brønsted acidity, thereby converting at least a portion of the 1,4-butanediol into tetrahydrofuran. In some embodiments, the catalyst composition has substantially only Lewis acidity determinable from IR absorption spectra of pyridine adsorbed on the catalyst. In some other embodiments, the gamma-alumina contains substantially no stabilizers.

These processes are advantageous in that they result in the synthesis of THF in high yield and high purity by hydrogenation and hydrogenolysis of maleic and succinic diesters (usually dimethyl maleate (DMM) and succinate (DMS)) and the resultant BDO over Cu-containing catalysts in the gas phase. That is the reaction begins with DMM, which undergoes hydrogenation to DMS. Then, the DMS undergoes hydrogenolysis to GBL, BDO, and then THF. The THF fraction may be more than 10 mol % as a proportion of the target products.

There are many variants to the methods described, which often parallel the various embodiments of the catalyst. Thus, in some embodiments, the amount of silica is varied. For example, in one embodiment, the catalyst composition comprises less than about 1 wt % silica, less than about 0.5 wt % silica, less than about 0.25 wt % silica, less than about 0.1 wt % silica. In yet other embodiments, the catalyst composition comprises substantially no silica. The amount of copper oxide can also be varied. For example, the catalyst composition can contain from about 3 to about 30, or about 10 to about 15 wt % copper oxide.

Typical reaction conditions for this stage of the overall process, as well as for the previous stages are as follows. The hydrogenation and hydrogenolysis of dimethyl maleate to 1,4-butandiol is performed in the gas phase. The diester stream is vaporized in a hydrogen-containing gas stream under reaction pressure at temperatures of about 150 to about 220° C. The vapors are passed over the catalysts. The molar ratio of hydrogen in the reactant present in the reactor before the hydrogenation catalyst to diester is in the range from about 50 to about 500:1, specifically from about 60 to about 400:1, and more specifically from about 70 to about 300:1. The hydrogenation can be operated with hydrogen recycling (circulation gas). The hydrogen consumed in the reaction, plus that removed via off-gas and gas removed via effervescence, is replenished continually in the form of fresh hydrogen. The molar ratio of fresh hydrogen to diester here is generally from about 3.5 to about 10:1, specifically from about 4 to about 8:1, and more specifically from about 5 to about 7:1.

The reaction conditions of the dehydration and ring closure of 1,4-butanediol to THF can include pressures in the range from about 10 to about 100 bar, specifically from about 20 to about 80 bar, and more specifically about 30 to about 60 bar. The reaction temperatures can be selected to be from about 150 to about 300° C., specifically from about 155 to about 250° C., and more specifically from about 160 to about 230° C. In some embodiments, there is an increase in reaction temperature in the reactor during the reaction.

There are several arrangements of the catalysts for the hydrogenation/hydrogenolysis to 1,4-butanediol and dehydration/ring closure to THF. A common setup for these catalysts is a fixed bed reactor with the catalyst compositions in pelletized form. There is usually a layer of the catalyst that produces BDO over the catalyst for THF synthesis from BDO. There is often an additional protective layer over the top layer, because leftover acid from an initial esterification reaction can affect the performance of the Cu catalyst. One such protective layer comprises copper and chromium. Thus, the final configuration features the protective layer over the BDO synthesis catalyst layer, which in turn overlies the THF synthesis catalyst. Another configuration for the catalysts is to have the protective layer over the BDO synthesis catalyst in one fixed bed reactor, and the THF synthesis catalyst in another side reactor. In one or more embodiments which relate to a 2-part reaction system, a second catalyst may also have a protective layer.

As discussed above, the reaction of DMM to BDO can take place over a copper-manganese-alumina catalyst. The reaction of BDO to THF is carried out over a copper-alumina catalyst of the type described herein. The two reactions may take place sequentially in one reactor, with staged catalyst beds, or in two separate reactors. Specifically, the catalysts may be present in layers all in one reactor or in two or more reactors. An example of the latter setup comprises the first catalyst in the first reactor and the second catalyst in a second reactor.

Accordingly, another aspect of the invention relates to a catalyst system for the synthesis of tetrahydrofuran from maleic anhydride, the system comprising a first catalyst composition effective to convert dimethyl maleate and dimethyl succinate to 1,4-butanediol and methanol; and a second catalyst composition comprising about 3 to about 50 wt % copper oxide on a gamma-alumina support, wherein the catalyst composition comprises less than about 1.5 wt % silica, and with the proviso that the catalyst composition has Lewis acidity and no Brønsted acidity. The catalyst composition can be modified as discussed above. For example, in one embodiment, the catalyst composition has substantially only Lewis acidity determinable from IR absorption spectra of pyridine adsorbed on the catalyst. In another embodiment, the gamma-alumina contains substantially no stabilizers.

In one or more embodiments, the first and second catalyst compositions are in pellet form in a fixed bed reactor. In a further embodiment, the fixed bed reactor contains a layer of the first catalyst composition over a layer of the second catalyst composition. There is often an additional protective layer over the top layer, because leftover acid from the esterification reaction can affect the performance of the first catalyst. Thus, in one embodiment, the catalyst system further comprises a protective layer over the layer of the first catalyst composition. One such protective layer comprises copper and chromium.

In an alternative embodiment, the first and second catalyst compositions are in pellet form in separate reactors. In a further embodiment, the catalyst system further comprises a protective layer over the first catalyst composition. In yet even further embodiments, the protective layer comprises copper and chromium.

EXAMPLES

Preparation of Catalysts

Example 1

Catalyst 1 was prepared on gamma-alumina via the incipient wetness technique using an aqueous solution of 16 wt % $Cu(NO_3)_2$. The Cu containing catalyst was dried and then calcined to decompose the nitrate to the oxide. The resulting catalyst contained 11% CuO. In the reactor, the catalyst was reduced in a stream containing hydrogen to obtain metallic Cu before use.

Example 2 (Comparative)

Catalyst 2 was prepared the same way as Example 1 but the gamma-alumina was physically mixed with 5 wt % of HZSM-5 (zeolitic crystals). It is considered comparative because the HZSM-5 adds Brønsted acidity to the catalyst composition.

Example 3

Catalyst 3 was prepared the same way as Example 1, but the gamma alumina contained 1.33% $SiO_2$.

Acidity Testing

Sample Preparation and Analysis

The acidity test was done with an FTIR of adsorbed pyridine. The sample was ground to <10 micron particle size just prior to analysis to limit intake of moisture and contaminants. The sample was placed directly on the heated post in the Spectra Tech Controlled Environment Chamber (CEC), and leveled with a spatula, but not packed down. Any spills were cleaned with a pipette or miniature vacuum cleaner, as any loose powder can get into the gas flow lines and/or the o-ring, which could cloud future data. The cover was screwed on, making sure the windows were clean and uncracked.

The instrument parameters were set as follows:
Resolution: 2 cm$^{-1}$
scan range: 4000-1300 cm$^{-1}$, expand 1700-1400 cm$^{-1}$ The cell height (CEC) was aligned to maximize the IR energy throughput. A quick scan was carried out to make sure there is a signal between 1800 and 1400 cm$^{-1}$. The gain was set so that the signal was at maximum but all still on scale. For the Perkin-Elmer with the MCT detector, a gain of one should give an energy of about 4400 cm$^{-1}$. This is 10% of the beam energy. A single beam monitor should give a "valid" throughput from 4000 to 1300 cm$^{-1}$ (regardless of the gain).

Before beginning the run, the following was checked:
water supply (approximately 2 gallons are needed per run).
water flow (20 ml/min).
gas flow (50 ml/min).
The indicating tube on the Supelco® drier did not turn brown.

The sample was then heated and dried. The sample was occasionally scanned to make sure the IR signal was still present. Note that heating externally may change the results obtained, as it may change the surface OH groups. This must be determined for each sample.

After the heating was completed, the sample was cooled to approximately 40° C. so that the background spectrum could be obtained. The 1640 cm$^{-1}$ region was checked to ensure all water was gone. The background spectrum of the dried sample was collected and saved.

Pyridine was then added. With the instrument scanning against the background just collected the valves surrounding the pyridine reservoir were opened to let nitrogen gas flow through the pyridine. They were left open until the pyridine spectrum was seen on the IR screen, which was approximately 10 seconds. The pyridine was closed off, leaving the nitrogen flow on.

Equilibration was achieved by removing excess pyridine from the gas lines and the sample. This was accomplished by leaving the sample sitting for 30 minutes with the cell at 40° C. A scan of the sample was taken at 40° C. after equilibration.

Data Analysis

Quantitative interpretation required data reduction with use of a peak fitting/deconvolution software and extinction coefficient for the type of sample in use. K-Munk correction, which converts data such that peak intensity will be linear with concentration, was used. Following the manufacturer's instructions, K-Munk was applied on the final spectrum collected and the resultant units were in K-Munk.

Peak areas are calculated using a peak-fitting program and with determined extinction coefficients, dependent on sample type, IR peak areas are quantifiable into moles/gram of Lewis or Brønsted acidity for a given sample.

For zeolites and alumina materials, extinction coefficients were determined to be 6.09 for Lewis and 9.32 Brønsted acid-sites. Baseline corrected peak area measurement in absorbance is obtainable at 1546 cm$^{-1}$ for the Brønsted peak and 1450/1455 cm$^{-1}$ for Lewis peak. The following calculation is used:

$$\frac{\text{Corrected baseline peak area}}{9.32 \text{ (Bronsted) or } 6.09 \text{ (Lewis)}} \times 1000 =$$

acid site measurement in µmoles/gram

The results are shown below in Table 1, and values are given as µmol/g.

TABLE 1

Types of Acidity In Examples 1-3

| Catalyst | Lewis acidity (µmole/g) | Brønsted acidity (µmole/g) |
|---|---|---|
| Catalyst 1 | 537 | 0 |
| Catalyst 2 | 1089 | 11 |
| Catalyst 3 | 1092 | 0 |

As shown in Table 1, Examples 1 and 3 did not exhibit Brønsted acidity, although all of the examples had Lewis acidity to varying degrees.

Performance Testing

The above catalysts were tested in a flow reactor at 185° C., 195° C., and 205° C. The feed mixture was comprised of 31% methanol, either 2% or 4% butanol, 7% gamma butyrolactone, 55% BDO, and 1% water. Each of the catalysts was tested for BME and DME production. Table 2 below shows the formation of BME, given as GC peak area %. Table 3 below shows the formation of DME values, also given as GC peak area %.

TABLE 2

BME Production in Examples 1-3 as GC Peak Area %

| Butanol, % | TEMP, ° C. | Example 1 (GC Peak Area %) | Example 2 (GC Peak Area %) | Example 3 (GC Peak Area %) |
|---|---|---|---|---|
| 2 | 185 | 0.25 | 1.6 | 0.65 |
| 2 | 195 | 0.55 | 1.8 | 0.65 |
| 2 | 205 | 1.1 | 1.7 | 1.8 |
| 4 | 185 | 0.35 | 1.8 | 0.75 |
| 4 | 195 | 1.4 | 3.0 | 1.7 |

TABLE 3

DME Production in Examples 1-3 as GC Peak Area %

| Butanol, % | TEMP, ° C. | Example 1 | Example 2 | Example 3 |
|---|---|---|---|---|
| 2 | 185 | 0.17 | 0.95 | 0.45 |
| 2 | 195 | 0.55 | 2.4 | 0.7 |
| 2 | 205 | 1.1 | 2.1 | 1.5 |
| 4 | 185 | 0.2 | 1.1 | 0.5 |
| 4 | 195 | 0.3 | 1.3 | 0.75 |

The tests showed that Example 2, which was the comparative example, produced the greatest amount of both BME and DME. On the other hand, Examples 1 and 3 produced less BME and DME, with Example 1 producing the least amount of BME and DME. Thus, the examples that did not contain Brønsted acidity produced less of the usually undesired BME and DME byproducts than did the example that did contain Brønsted acidity.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments. The order of description of the above method should not be considered limiting, and methods may use the described operations out of order or with omissions or additions.

It is to be understood that the above description is intended to be illustrative, and not restrictive. Many other embodiments will be apparent to those of ordinary skill in the art upon reviewing the above description. The scope of the invention should, therefore, be determined with reference to the appended claims, along with the full scope of equivalents to which such claims are entitled.

The invention claimed is:

1. A method of synthesizing tetrahydrofuran, the method comprising:
   contacting a stream comprising 1,4-butanediol with a catalyst composition consisting of about 3 to about 50 wt % copper oxide, based upon the total weight of the catalyst composition prior to a catalyst activation, on a gamma-alumina support having less than about 1.5 wt % silica, and thereby converting at least a portion of the 1,4-butanediol into tetrahydrofuran;
   wherein:
   with the proviso that the catalyst composition has Lewis acidity and no Brønsted acidity;
   the Lewis acidity is confirmed by an IR absorption peak at about 1450-1455 $cm^{-1}$ in an IR spectra of pyridine adsorbed on the catalyst;
   the Brønsted acidity is confirmed by the lack of an IR absorption peak at about 1546 $cm^{-1}$ in an IR spectra of pyridine adsorbed on the catalyst; and
   the gamma-alumina is free of stabilizers.

2. The method of claim 1, wherein the catalyst composition has less than about 1 wt % silica.

3. The method of claim 2, wherein the catalyst composition has less than about 0.5 wt % silica.

4. The method of claim 3, wherein the catalyst composition is free of silica.

5. The method of claim 1, wherein the catalyst composition contains from about 5 to about 20 wt % copper oxide.

6. The method of claim 1, further comprising reducing the CuO to copper metal prior to contacting the catalyst composition with a stream comprising 1,4-butanediol.

* * * * *